(12) United States Patent
Hopkinson et al.

(10) Patent No.: US 10,323,125 B1
(45) Date of Patent: Jun. 18, 2019

(54) POLYMER FOR CARBON DIOXIDE CAPTURE AND SEPARATION

(71) Applicant: Energy, United States Department of, Washington, DC (US)

(72) Inventors: David Hopkinson, Morgantown, WV (US); Ali Kemal Sekizkardes, Pittsburgh, PA (US)

(73) Assignee: U.S. Department of Energy, Washington, DC (US)

( * ) Notice: Subject to any disclaimer, the term of this patent is extended or adjusted under 35 U.S.C. 154(b) by 182 days.

(21) Appl. No.: 15/625,015

(22) Filed: Jun. 16, 2017

Related U.S. Application Data

(60) Provisional application No. 62/350,779, filed on Jun. 16, 2016.

(51) Int. Cl.
| | |
|---|---|
| C08G 73/06 | (2006.01) |
| C08F 34/00 | (2006.01) |
| B01D 53/02 | (2006.01) |
| B01D 53/62 | (2006.01) |
| B01D 53/96 | (2006.01) |
| B01D 69/14 | (2006.01) |
| C07D 235/04 | (2006.01) |
| C07D 403/02 | (2006.01) |

(52) U.S. Cl.
CPC ......... *C08G 73/0677* (2013.01); *B01D 53/02* (2013.01); *B01D 53/62* (2013.01); *B01D 53/96* (2013.01); *B01D 69/148* (2013.01); *C07D 235/04* (2013.01); *C07D 403/02* (2013.01); *C08F 34/00* (2013.01); *B01D 2253/202* (2013.01); *B01D 2253/308* (2013.01); *B01D 2257/504* (2013.01); *B01D 2325/12* (2013.01); *C08F 2500/24* (2013.01)

(58) Field of Classification Search
CPC .. B01D 46/0036; B01D 53/02; B01D 53/025; B01D 53/04; B01D 2257/504; B01D 2253/202; B01D 2253/206; B01D 2253/25; B01D 2253/306; B01D 2253/308; B01D 2253/31; B01J 20/26–20/208; B01J 20/28054; B01J 20/28057; B01J 20/28088; B01J 20/28097
USPC .............................. 96/108, 153, 154; 95/139
See application file for complete search history.

(56) References Cited

PUBLICATIONS

Altarawneh et al. ("New insights into carbon dioxide interactions with benzimidazole-linked polymers" Chem. Commun., 2014, 50, 3571-3574, Published Feb. 11, 2014) (Year: 2014).*

(Continued)

*Primary Examiner* — In Suk C Bullock
*Assistant Examiner* — Jason Y Chong
(74) *Attorney, Agent, or Firm* — Jacob A. Heafner; Michael J. Dobbs; Brian J. Lally

(57) ABSTRACT

One or more embodiments relate to providing substrate for separating a first gas component from a gaseous mixture, said substrate comprising a benzimidazole-linked polymer. Also provided is a method for synthesizing a substrate for separating a first gas component from a gaseous mixture, the method comprising performing a free condensation reaction between an aryl-o-diamine and an aryl-aldehyde to yield a benzimidazole-linked polymer. Other embodiments related to providing a $CO_2$ separation membrane comprising benzimidazole-linked polymer residing within a matrix.

17 Claims, 11 Drawing Sheets

(56) References Cited

PUBLICATIONS

Altarawneh et al. ("Highly porous and photoluminescent pyrene-quinoxaline-derived benzimidazole-linked polymers" J. Mater. Chem. A, 2015, 3, 3006-2010, Published on Dec. 16, 2014) (Year: 2014).*

Rabbani et al. ("Template-Free Synthesis of a Highly Porous Benzimidazole-Linked Polymer for CO2 Capture and H2 Storage" Chem. Mater. 2011, 23, 1650-1653) (Year: 2011).*

Rabbani et al. ("Synthesis and Characterization of Porous Benzimidazole-Linked Polymers and Their Performance in Small Gas Storage and Selective Uptake" Chem. Mater. 2012, 24, 1511-1517) (Year: 2012).*

Rabbani et al. ("High CO2 uptake and selectivity by triptycene-derived benzimidazole-linked polymers" Chem. Commun., 2012, 48, 1141-1143) (Year: 2012).*

Sekizkardes et al. ("Application of pyrene-derived benzimidazole-linked polymers to CO2 separation under pressure and avcuum swing adsorption settings" J. Mater. Chem. A, 2014, 2, 12492-12500) (Year: 2014).*

Altarawneh et al. ("Effect of Acid-Catalyzed Formation Rates of Benzimidazole-Linked Polymers on Porosity and Selective CO2 Capture from Gas Mixtures" Environ. Sci. Technol. 2015, 49, 4715-4723) (Year: 2015).*

\* cited by examiner

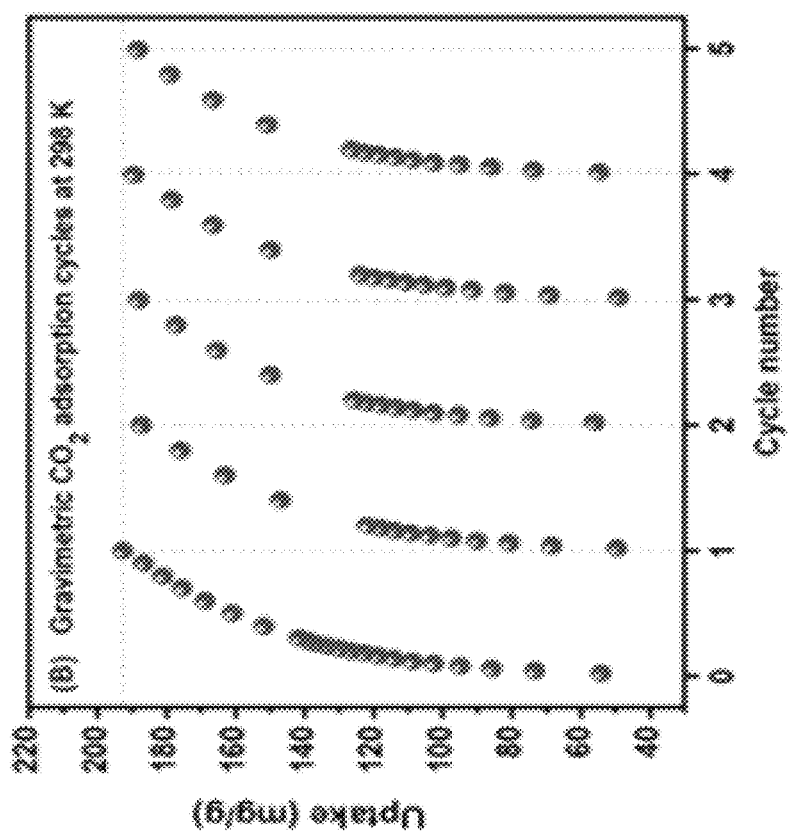
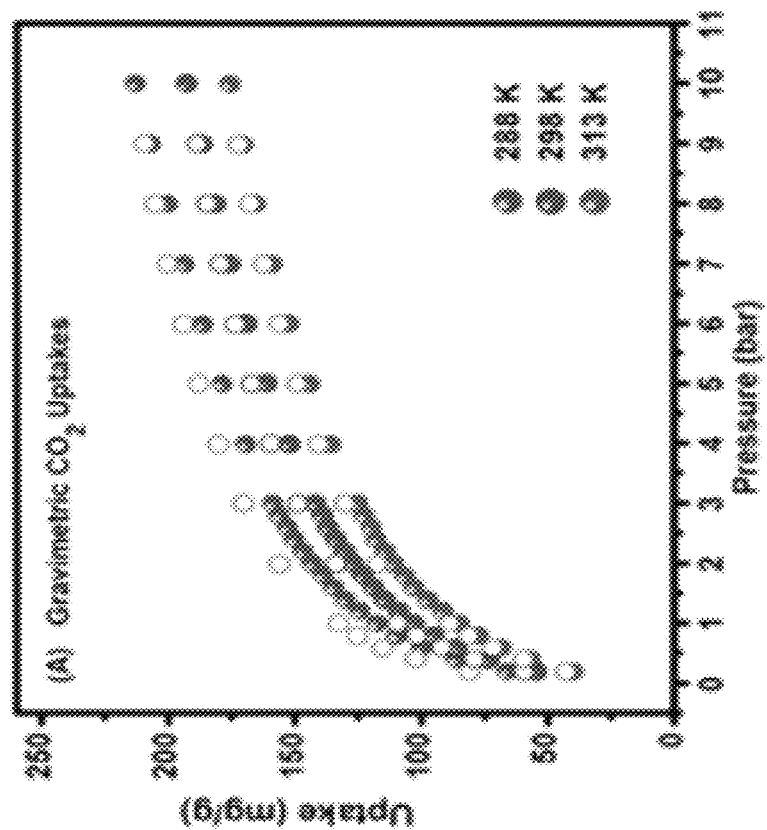
FIG. 4B
FIG. 4A

FIG. 5

| Sorbent | $\Delta N_1$ | R | $\alpha_{12}^{ads}$ | S |
|---|---|---|---|---|
| BILP-101 (POP) | 0.80 | 84.8 | 70.3 | 556 |
| SNU-Cl-va (POP) | 0.41 | 87.3 | 38.0 | 262 |
| Zeolite-13X (Zeolite) | 1.35 | 54.2 | 86.2 | 128 |
| ZIF-78 (MOF) | 0.58 | 96.3 | 34.5 | 396 |
| ZIF-82 (MOF) | 0.38 | 92.5 | 22.7 | 101 |
| MOF-4b (MOF) | 0.06 | 83.8 | 154 | 104 |
| HKUST-1 (MOF) | 0.55 | 89.0 | 20.4 | 46.2 |
| Ni-MOF-74 (MOF) | 3.20 | 73.7 | 41.1 | 83.5 |
| NoritR1 extra (Activated Carbon) | 0.28 | 73.7 | 10.7 | 5.09 |

$\Delta N_1$= $CO_2$ working capacity (mol/kg), R= Regenerability, $\alpha_{12}^{ads}$= IAST selectivity, S=Sorbent selection parameter (Eq. S3).

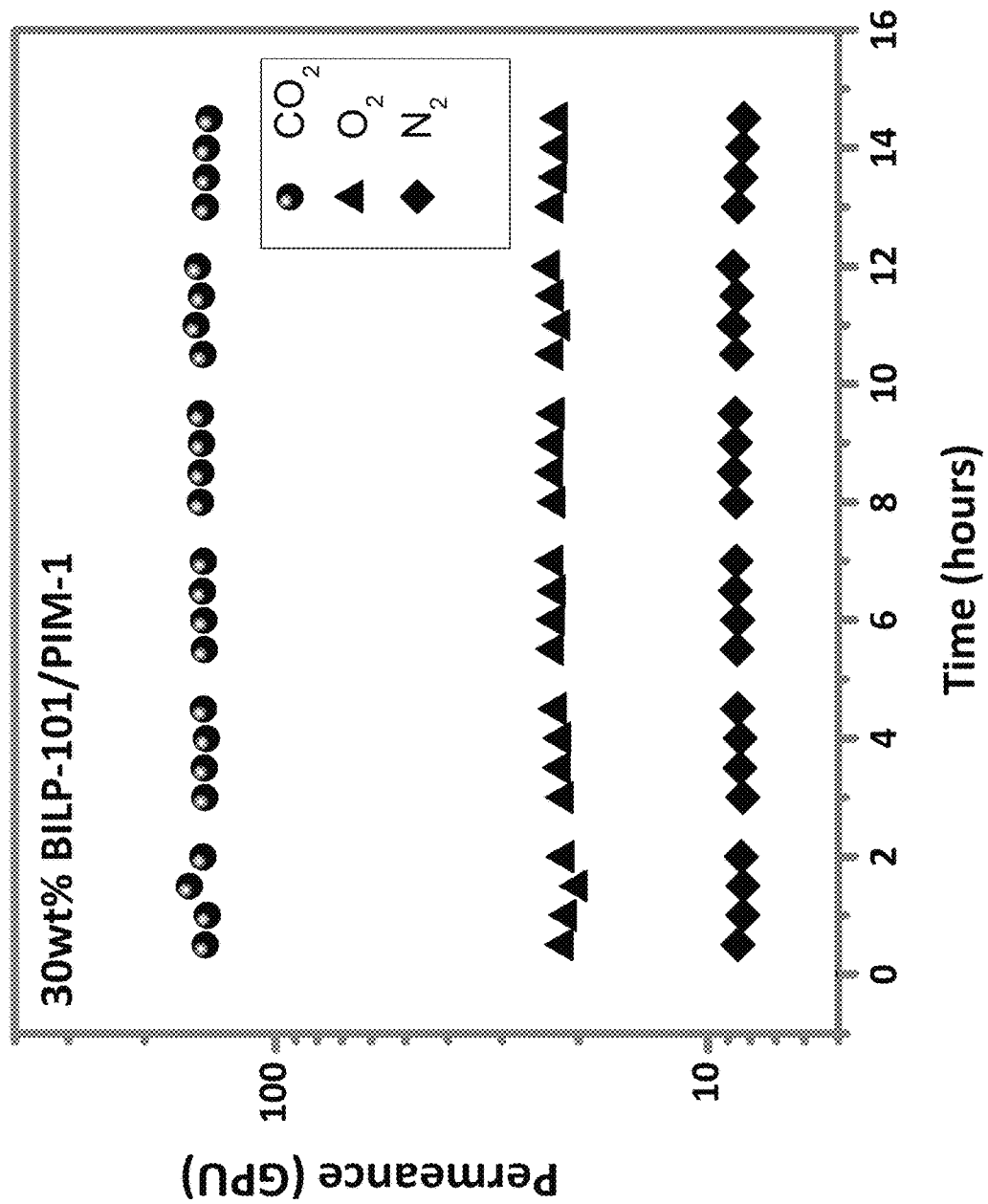

POLYMER FOR CARBON DIOXIDE CAPTURE AND SEPARATION

CROSS REFERENCE TO RELATED APPLICATION

This utility patent application claims the benefits of U.S. Provisional Application No. 62/350,779, filed on Jun. 16, 2016, the entirety of which is incorporated herein by reference.

STATEMENT REGARDING FEDERALLY SPONSORED RESEARCH AND DEVELOPMENT

The United States Government has rights in this invention pursuant to an employer/employee relationship between the inventors and the U.S. Department of Energy, operators of the National Energy Technology Laboratory (NETL).

FIELD OF THE INVENTION

This invention relates to carbon dioxide sorbents and more specifically, this invention relates to a polymer and method for making the polymer having enhanced $CO_2$ separation capabilities.

BACKGROUND OF THE INVENTION

Carbon dioxide ($CO_2$) capture embodies ongoing research. The ultimate goal in $CO_2$ sequestration is to first capture it, then redirect it to a long term storage paradigm.

Solid sorbents have been envisioned for capture of $CO_2$ and other targeted moieties. Such sorbents include zeolites, porous carbon, organic molecular crystals, and metal organic frameworks (MOFs). But these state of the art adsorbents exhibit poor chemical and thermal stability, particularly under practical $CO_2$ capture processes which embody low $CO_2$ concentrations (e.g., below about 20 percent). Examples of the shortcomings of the prior art include the following:

Low $CO_2$ uptake or/and high $CO_2$ uptake with additional energy requirement at the desorption step.

Low $CO_2$ separation performance over other gasses present in the gas stream

High energy output to release captured $CO_2$

Complex material design and preparation.

Efforts to create polymeric adsorbents continue to fall short. One of the drawbacks experienced is the generation of soluble oligomers due to inefficient cross linking between reactants (e.g., benzene and tetrahydrochloride). Also, many methods require metal catalysts which require their removal during product purification.

Furthermore, pore size distribution of the best state of the art adsorbents are no less than 0.68. (Pore size distribution is average spherical pore size. It is determined by fitting $N_2$ adsorption isotherms (collected at 77 K) of materials. Non local density functional theory calculates the pore size distribution based on the isotherm.) This state of the art pore size distribution value is too large (pores are too wide) to enable the surface energies necessary to adsorb target moieties at typical (i.e. low) flue concentrations.

Efforts have been made to combine microporous polymers with inorganic particles. These mixed matrix membranes were created to improve gas transport properties. However, many of these composites experience delamination such that voids form at the polymer-particle interface. This reduces gas selectivity.

A need exists in the art for a sorbent having much enhanced affinity for carbon dioxide at typical flue effluent concentrations. Strong interaction between $CO_2$ and the framework of the sorbent is needed due to the low partial pressure of $CO_2$ in flue gases. The sorbent should have a pore diameter of no greater than about 3 nm and preferably no greater than about 2 nm. The sorbent should exhibit narrow pore size distribution and a high percentage of functional sites for $CO_2$ capture and separation. A need also exists for a simple and inexpensive method to making the sorbent. For example, the method should employ a minimal number of steps and utilize relatively common reactants and be template free.

BRIEF SUMMARY OF INVENTION

An object of one or more embodiments is to provide a $CO_2$ adsorption polymer and a method for making the polymer that overcomes many of the drawbacks of the prior art.

Another object of one or more embodiments is to provide a polymer with superior $CO_2$ to $N_2$ adsorption. A feature of the invention is that the polymer has a pore size distribution of approximately 0.54 nm, and a permanent micro porosity of less than about 6 nm and preferably between approximately 0.5 nm and 2 nm. An advantage one or more embodiments is that the polymer provides optimal interaction energy within physisorption limits and high physicochemical stability. The narrow pores enable more attraction surface energy for $CO_2$ and more $CO_2$ selectivity over $N_2$.

Yet another object of one or more embodiments is to provide a benzimidazole-linked polymer synthesized from commercially available (e.g., widely used) building blocks (monomers). Features of one or more embodiments include providing enhanced Lewis basic nitrogen/carbon molar ratios of up to 68/24 (e.g., high concentrations of imidazole functionality), and smaller pore size with high micro porosity rather than high surface area. An advantage of the polymer is that it provides higher concentrations of interaction sites, thereby optimizing interaction energy for increased $CO_2$ uptake and higher polymerization yield, all with less by-product.

Still another object of one or more embodiments is to provide a mixed matrix membrane. One feature incorporates two microporous polymers such as a polymer of intrinsic microporosity and a benzimidazole linked polymer. An advantage of one or more embodiments is that the composite membrane has relatively higher mechanical stability (compared to state of the art membranes) with good interfacial interaction due to the hydrogen bonding capability of the constituent materials.

Another object of one or more embodiments is to provide a method for making highly efficient polymeric adsorbents. A feature of the method is the incorporation of a three-step process for generating the adsorbent, wherein the entire process occurs within a single reaction chamber. An advantage of this single reaction vessel protocol is that it facilitates purification of the final product. Another advantage of the single reaction vessel protocol is that it facilitates a template free reaction such that no inorganic molecules or metal particles are required to facilitate production of the invented adsorbent.

Still another object of one or more embodiments is to functionalize an invented adsorbent by incorporating it as a constituent as a composite adsorbent substrate. A feature of the invention is the combination of a porous benzimidazole-linked polymer with aliphatic amines, wherein the amines reside in the pores of the polymer. An advantage of the invention is that the adsorption efficiency of the composite is two-fold compared to that of neat polymer.

Yet another object of one or more embodiments is to provide a mixed matrix membrane. A feature of the invention is the combination of nanoparticles of porous organic polymers (POPs) with an organic host matrix. An advantage of this invention is that the particles are strongly attracted to the matrix, thereby mitigating any delamination or void formation seen in state of the art membranes.

Briefly, one or more embodiments provide substrate for separating a first gas component from a gaseous mixture, said substrate comprising a benzimidazole-linked polymer which has a high affinity to $CO_2$ and high $CO_2/N_2$ selectivity. For example, the substrate may have a pore size distribution no greater than about 0.60.

Also provided is a method for synthesizing a substrate for separating a first gas component from a gaseous mixture, the method comprising performing a free condensation reaction between an aryl-o-diamine and an aryl-aldehyde to yield a benzimidazole-linked polymer.

The invention also provides a $CO_2$ separation membrane comprising benzimidazole-linked polymer residing within a matrix.

BRIEF DESCRIPTION OF SEVERAL VIEWS OF THE DRAWINGS

The invention together with the above and other objects and advantages will be best understood from the following detailed description of the preferred embodiment of the invention shown in the accompanying drawings, wherein:

FIG. 4A is a graph showing CO2 uptakes of the invented polymer at different temperatures, in accordance with features of one or more embodiments of the present invention;

FIG. 4B is a graph showing CO2 adsorption rates of the invented polymer over a plurality of cycles, in accordance with features of one or more embodiments of the present invention;

FIG. 5 is a table of S factors for the invented polymer and state of the art adsorbents, in accordance with features of one or more embodiments of the present invention;

FIG. 7 is a chart showing permeance of a membrane, in accordance with features of one or more embodiments of the present invention.

DETAILED DESCRIPTION OF THE INVENTION

Figure 1A:
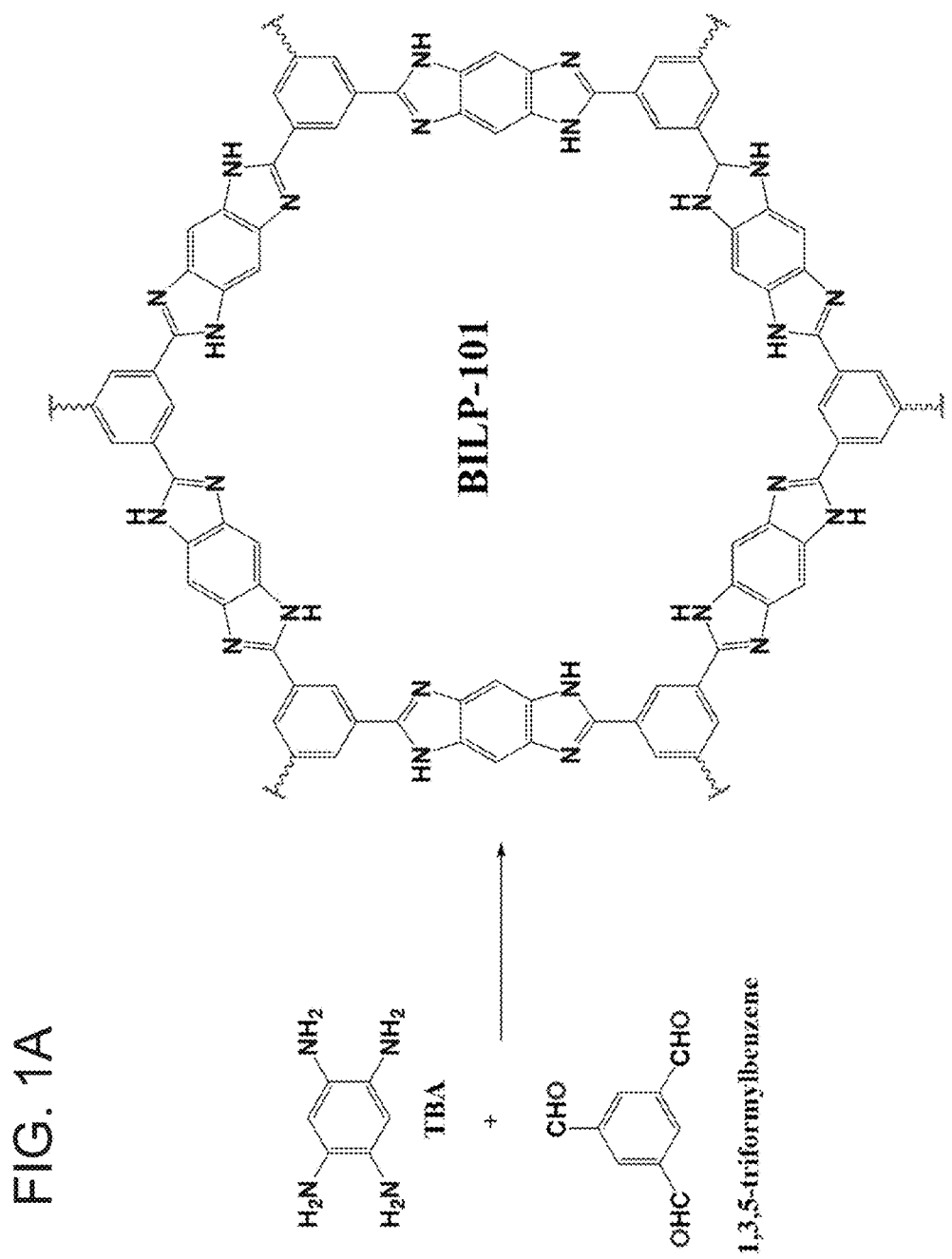
FIG. 1A is a reaction sequence of the production of a benzimidazole polymer, in accordance with features of one or more embodiments of the present invention.

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

One or more embodiments of the invention comprises the design and preparation of a new polymer in the polybenzimidazole class which provides enhanced uptake of $CO_2$. The high $CO_2$ uptake properties of the polymer may be explained by its ultra-micropores and high concentration of functional groups. Ultra-porosity, defined herein as pores with less than a 0.7 nm diameter, often less than 0.6 nm, and typically between 0.35 and 0.6 nm, is enabled by the invented method. Smaller pores means less distance between functional groups and this translates into high surface energy. Simultaneously, the utilization of imidazole reagent enhances the adsorption ability of the polymer inasmuch as six imidazole moieties combine with a single benzene ring. Imidazole groups have higher Lewis basicity compared to triazine, inasmuch as the later has its three nitrogen groups donating electrons in conjugation with benzene instead of adsorbing to $CO_2$. As such, higher concentrations (e.g., >0.5 bar) of $CO_2$ may be adsorbed with the invented structure.

The narrow pore size distribution (<1 nm) of the invented polymer enables the selective $CO_2$ capture characteristic over less polar gases such as $N_2$, $CH_4$ and $H_2$.

Described herein are three ways to apply the invented new polymer to scavenge selected moieties:

Neat;

Combined with an amine such that the amine resides within the pores of the new polymer; and Combined with an organic matrix such that the new polymer resides within a matrix to form a membrane. Inasmuch as the polymer bonds with, or otherwise chemically interacts with the invented polymer, the resulting membrane may be flexible, reversibly deformable, semi rigid, or rigid.

These three applications will be discussed separately infra.

Polymer Synthesis

Detail

The invented polymer is easily synthesized using different condensation polymerizations such as carboxylic acid functionalized aryl monomers. Examples of suitable monomers are the aryl-aldehydes selected from the group consisting of benzene-1,3,5-tricarbaldehyde, 4,4'4"-nitrillotribenzaldehyde, pyridine-2,6-dicarbaldehyde, N,N-diformylformamide, benzene-1,2,4,5-tetracarbaldehyde, 2,46-trihydroxybenzene-1,3,5-tricarbaldehyde and combinations thereof. Schiff base polymerization was utilized to generate various forms of the polymer.

Given its high porosity and rigid monomers, the invented polymer is amenable to pore modifications which can be easily tuned by changing the monomers through the same synthetic protocol. "Rigid" monomers are defined herein as those chemical structures that maintain their physical structure such that their chemical structure is less mobile. Therefore, the pores defined by the polymer remain intact over a range of temperatures and ranges. Rigidity as described herein does not mean that structures such as composites and membranes incorporating the invented polymers must be rigid or unbendable. Some such structures may in fact be reversibly deformable, as noted supra.

One or more embodiments of the invention provide for polymers having pores of all one diameter and density. Other embodiments of one or more embodiments of the invention enable a polymer having a plurality of pore sizes, for example within a nanometer in diameter of each other. This technique could be utilized to alter the pore size or the solubility for gases or other compounds. In addition to pore modifications, the chemical composition of the polymer may be adjusted to alternative applications by post-modification techniques.

One or more embodiments of the invention provide a simple and rationally designed polymer with commercial starting materials. It exhibits unprecedented and permanent ultra-micro porosity (≤6 nm). It has very high chemical (humidity/acid/base) and thermal (up to 600° C.) stability. The polymer exhibits the highest imidazole functionality content within a porous polybenzimidazole. Also, the polymer facilitates recyclable $CO_2$ adsorption without any thermal activation process.

One or more embodiments of the invented polymer exhibits the highest sorbent selection parameter (S factor) and the second highest Ideal Adsorbed Solution Theory (IAST) selectivity in over 40 sorbent candidates including MOFs, ZIFs, Zeolites, activated carbon studied under the same parameters (vacuum swing adsorption of $CO_2$ at 298 K. (See FIG. 5, discussed infra.)

Embodiments of the invented polymer are synthesized by a template-free polycondensation reaction between aryl-o-diamine and aryl-aldehyde. The invented method for producing the polymer provides a polymerization yield of greater than 90 percent, and with less by product, such as the liquid oligomers or metal catalysts discussed supra.

Embodiments of the invented polymer may be easily functionalized or modified for the target application. For example: FIG. 1C below shows two possible modifications of the polymer structure by employing different types of aryl-aldehyde and -amine monomers. Using Lewis basic aryl aldehyde monomers such as N,N-diformylformamide will increase the gas sorption properties of the final polymer. It is surmised that the incorporation of amine groups in the monomers provide more Lewis basic sites for target molecules such as $CO_2$. This increases the gas sorption properties of the final polymer. The invented polymer features imidazole functionalities which interact with acidic gases in a quadrupole dipole moment. The electrostatic force of interaction between the $CO_2$ molecules and the invented polymeric systems may be attributed to the dipole-quadrupole interaction.

Higher binding affinities can be conferred to the polymer by introducing more Lewis basic sites within its structure. For example, a monomer with a tertiary amine core supports higher CO2 uptake properties. This is because tertiary amines in imidazole have available lone pair for guest molecules such as $CO_2$. The lone pair of the other amine site of imidazole, which is the secondary amine, however, is employed in the conjugation of the benzimidazole ring. Therefore it is not available (the electron is shared with the conjugation), and so it is less Lewis basic compared to tertiary amines. Additional phenyl groups within the structure can potentially lead to higher interpenetration of polymer chains which affords smaller pore size and larger surface area. This is because additional phenyl groups increase the chance of interpenetration. The monomers bind to each other in less organized fashion due to different angles provided by each of the benzene rings.

Figure 1B:
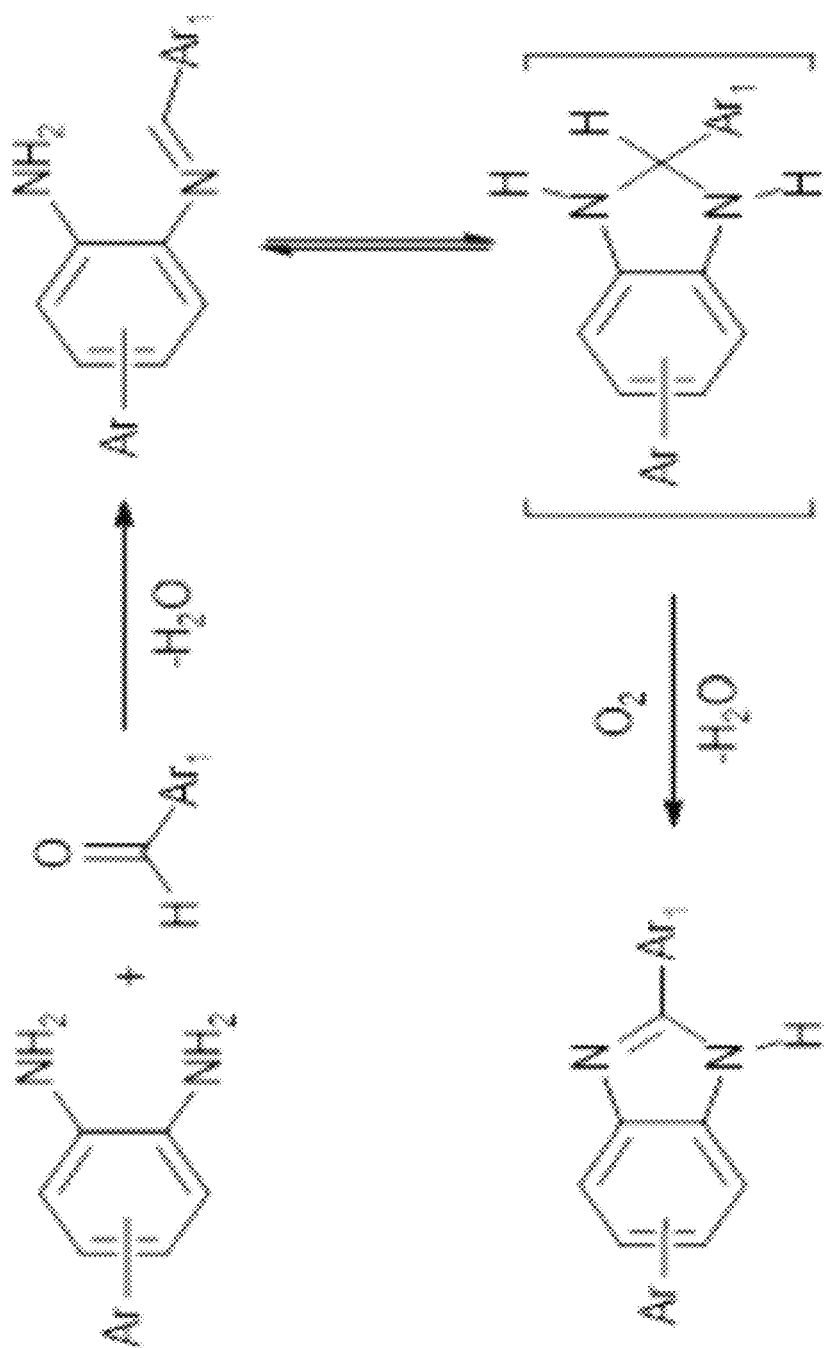
FIG. 1B is a schematic diagram of the condensation reaction of the method for producing adsorbent substrate, in accordance with features of one or more embodiments of the present invention.
Figure 1C:
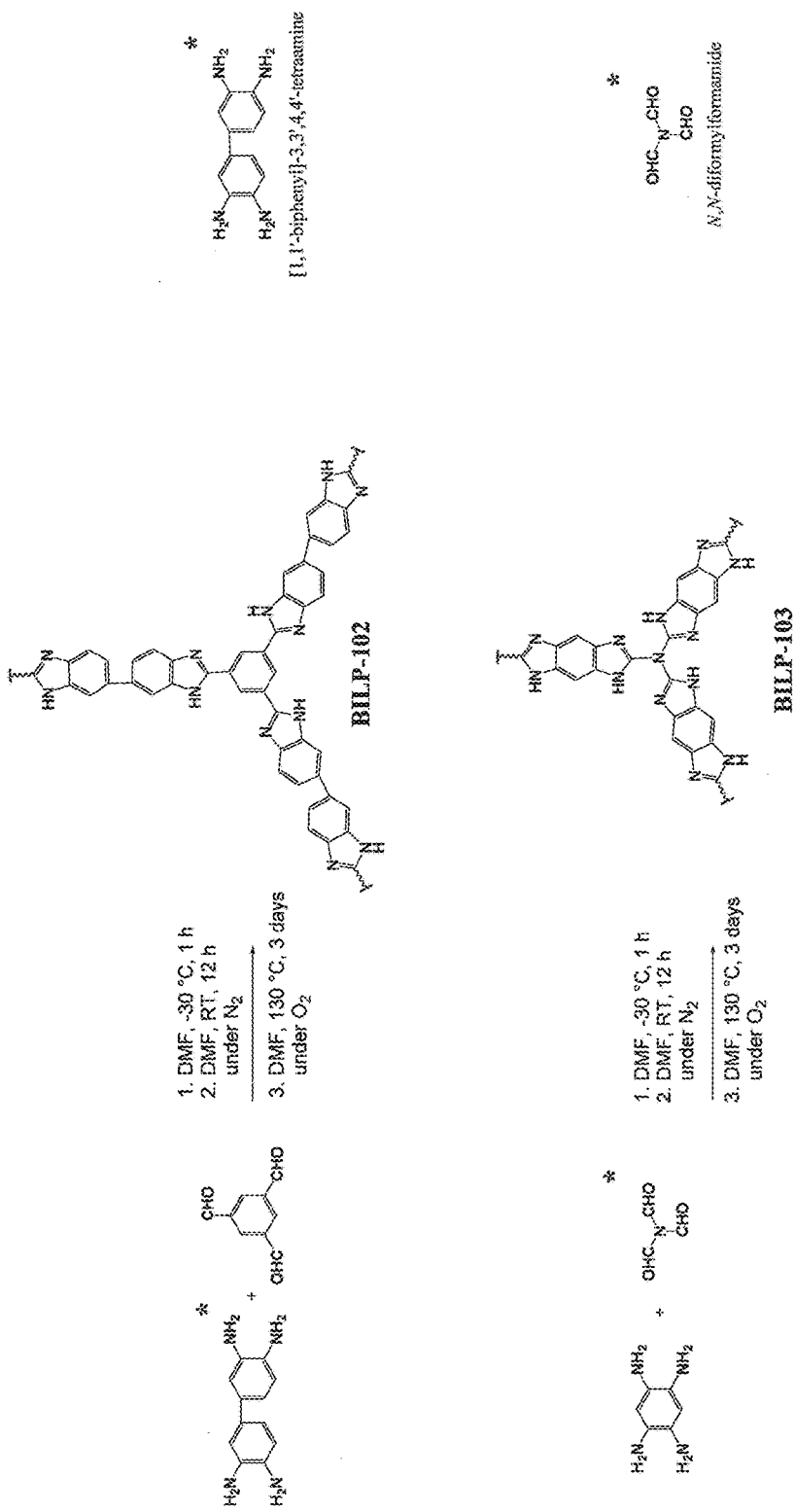
FIG. 1C is a reaction sequence of the production of two other benzimidazole polymers, in accordance with features of one or more embodiments of the present invention.

An embodiment of the invented polymer is depicted in FIG. 1A. The polymer is produced via a condensation reaction between 1,2,4,5-benzenetetramine tetrahydrochloride (TBA) and 1,3,5-triformylbenzene. Specifically, TBA reacts with triformylbenzene to produce the invented polymer. Mechanics of the condensation reaction are depicted in FIG. 1B. Specifically, imidazole is formed via a condensation reaction between 1,2-benzenediamine and arylaldehyde.

Example

An embodiment of the invented porous benzimidazole-linked polymer (hereinafter BILP) is poly[1,3,5-Tris(benzodimidazole) benzene and is depicted in FIG. 1A as BILP 101. It is synthesized by a template-free polycondensation reaction between commercially available aryl aldehyde and amine based monomers: The protocol in this example is merely illustrative inasmuch as other polymers BILP 102 and 103 may also be produced hereby, those other polymers depicted in FIG. 1C. Suitable monomers for modification of BILP 101 include 1,1'-biphenyl]-3,3'4,4'-tetraamine to produce BILP 102. (The second monomer in the BILP-102 protocol is 1,3,5 triformylbenzene.)

Suitable monomers for modification of BILP 101 include N,N-diformylformamide to product BILP 103. The first monomer in the BILP 103 protocol is 1,2,4,5-benzenetetramine tetrahydrochloride.

1,2,4,5-benzenetetramine tetrahydrochloride was mixed with anhydrous DMF and homogenized. The resultant homogeneous solution was cooled (e.g. to about minus 30° C.) and treated drop-wise with 1,3,5-triformylbenzene dissolved in anhydrous DMF. The temperature was maintained around minus 30° C. for 1 hour during which a dark brown solid formed.

The resultant slurry solution was left to warm to room temperature overnight. The flask containing the reaction mixture was flushed with air and capped tightly. The reaction mixture was then transferred to a static oven and heated gradually to above the boiling point of water (e.g. to 130° C.) and maintained thereby to afford a fluffy light brown powder. The solid was isolated by filtration (e.g., over a medium glass frit) and was subsequently washed with DMF, acetone, water, 1 M HCl, 1 M NaOH, water, and acetone. After filtration, the product was dried at 120° C. under vacuum to give BILP-101 as a fluffy light brown powder yield 92%). Anal. Calc. for $C_{36}H_{30}N_{12}.6H2O$: C, 68.50%; H, 4.70%; N, 26.60%. Found: C, 68.26; H, 3.96%; N, 23.77%.

Figure 2:
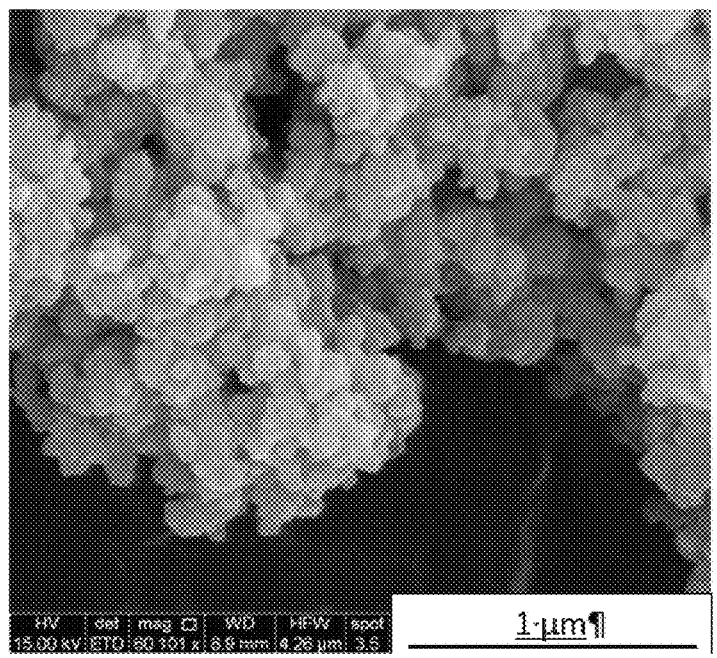
FIG. 2 is a photomicrograph of the polymer structurally depicted in FIG. 1A.

The resulting polymer, depicted in FIG. 2, displayed an ultra microporosity of less than about 0.6 nm and preferably less than about 0.54 nm and high chemical and thermal stability. High chemical stability can be determined by washing the polymer with about 0.1 M HCl and NaOH after which the polymer's properties remain intact. Thermogravimetric Analysis (TGA) of the polymer shows that polymer does not lose its weight by heating up to 500° C. and after exceeding 500° C., the significant weight change occurs. This analysis shows that the polymer is thermally stable up to and exceeding 500° C.

Neat Polymer

Adsorption Results

The invented polymer utilized alone provided very high $CO_2$ uptake (~1 mmol/g, 4-5 wt %) at 0.15 bar and 298 K. Its $CO_2/N_2$ selectivity is greater than 70 (and typically at between 80 and 90) at 298 K. The selectivity is attainable at temperatures ranging from about 258 K to about 313 K.

Figure 3A:
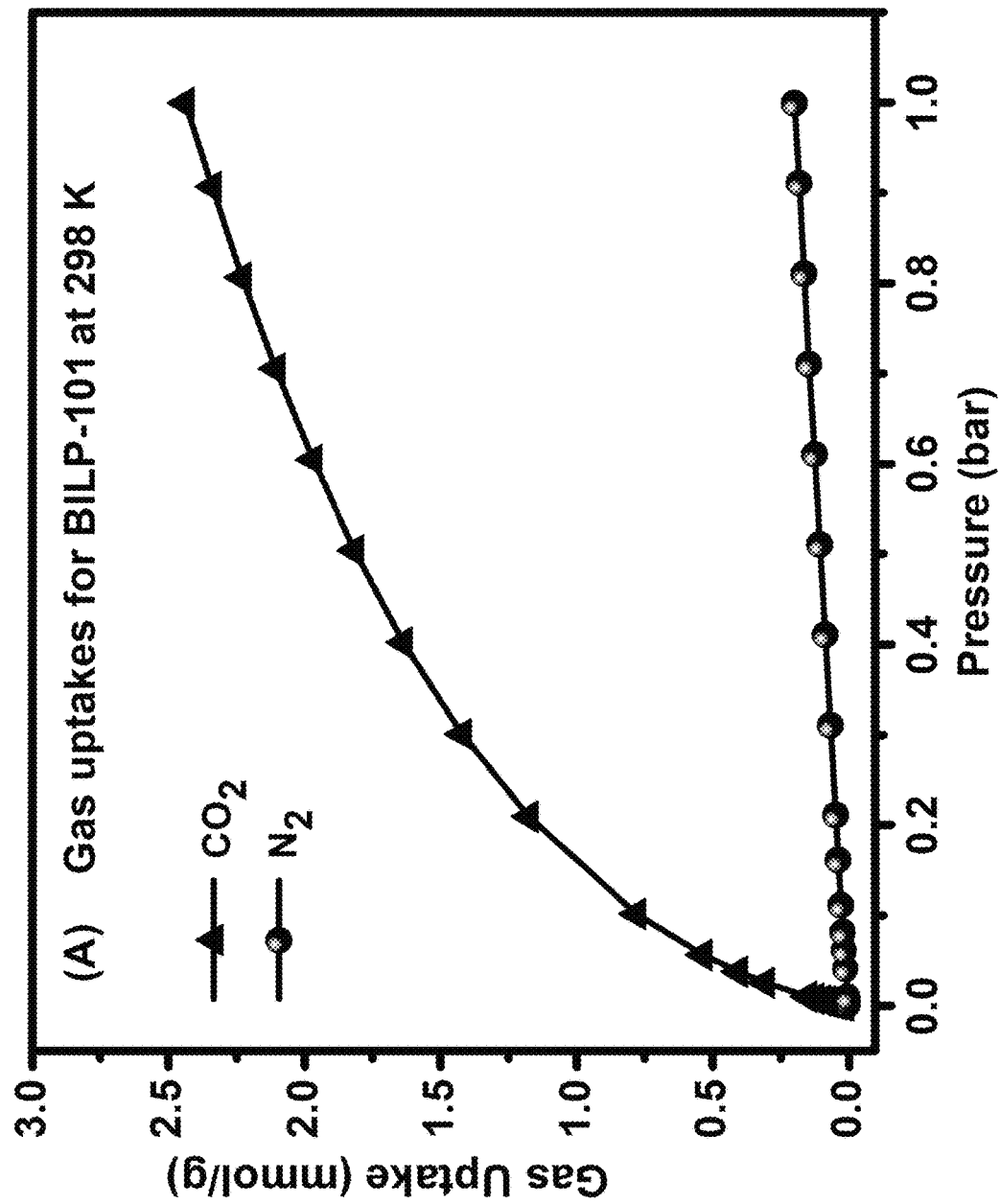
FIG. 3A is a graph depicting $CO_2$ and $N_2$ uptakes; in accordance with features of one or more embodiments of one or more embodiments of present invention.
Figure 3B:
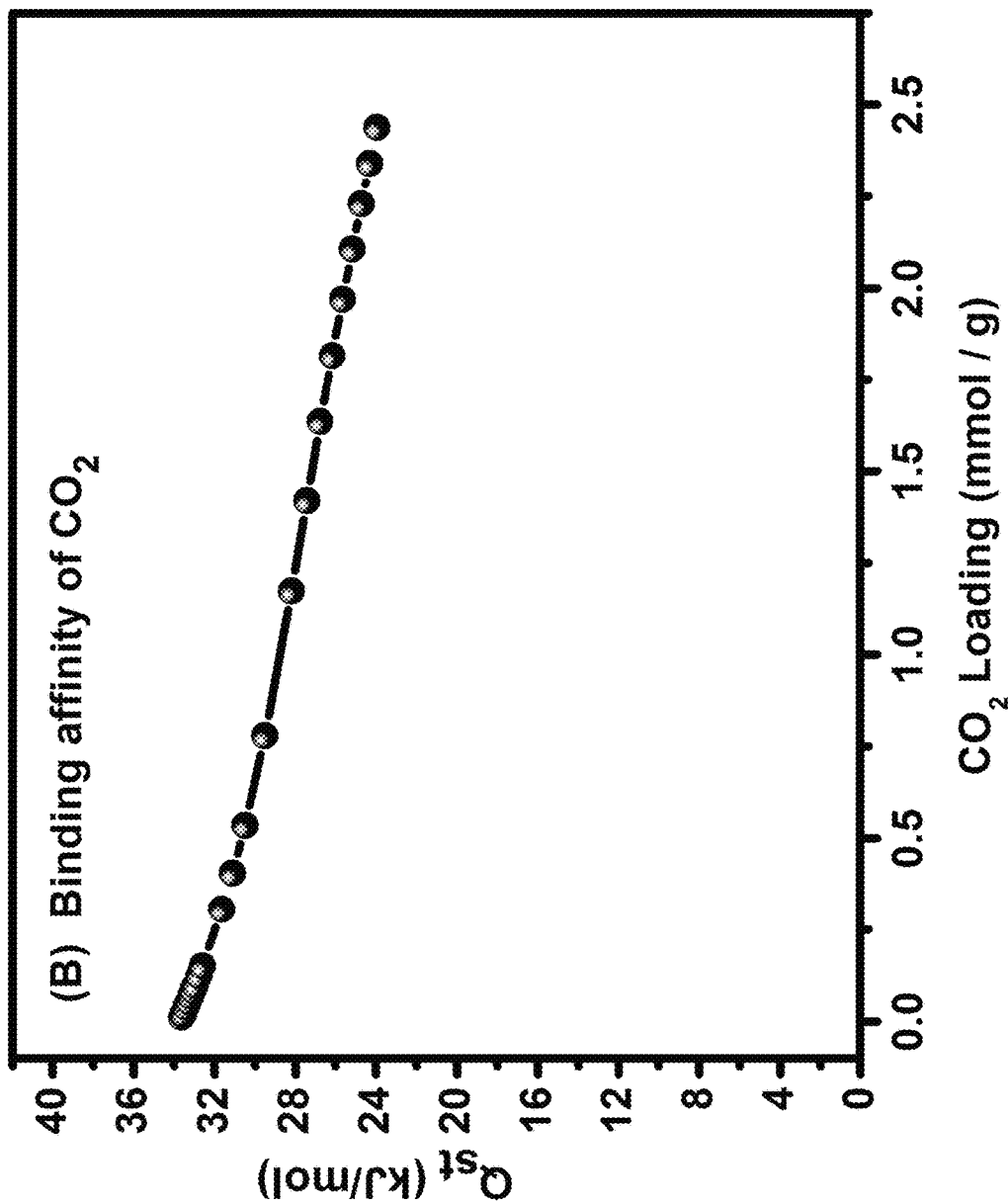
FIG. 3B is a graph depicting binding affinity for $CO_2$, in accordance with features of one or more embodiments of the present invention.
Figure 3C:
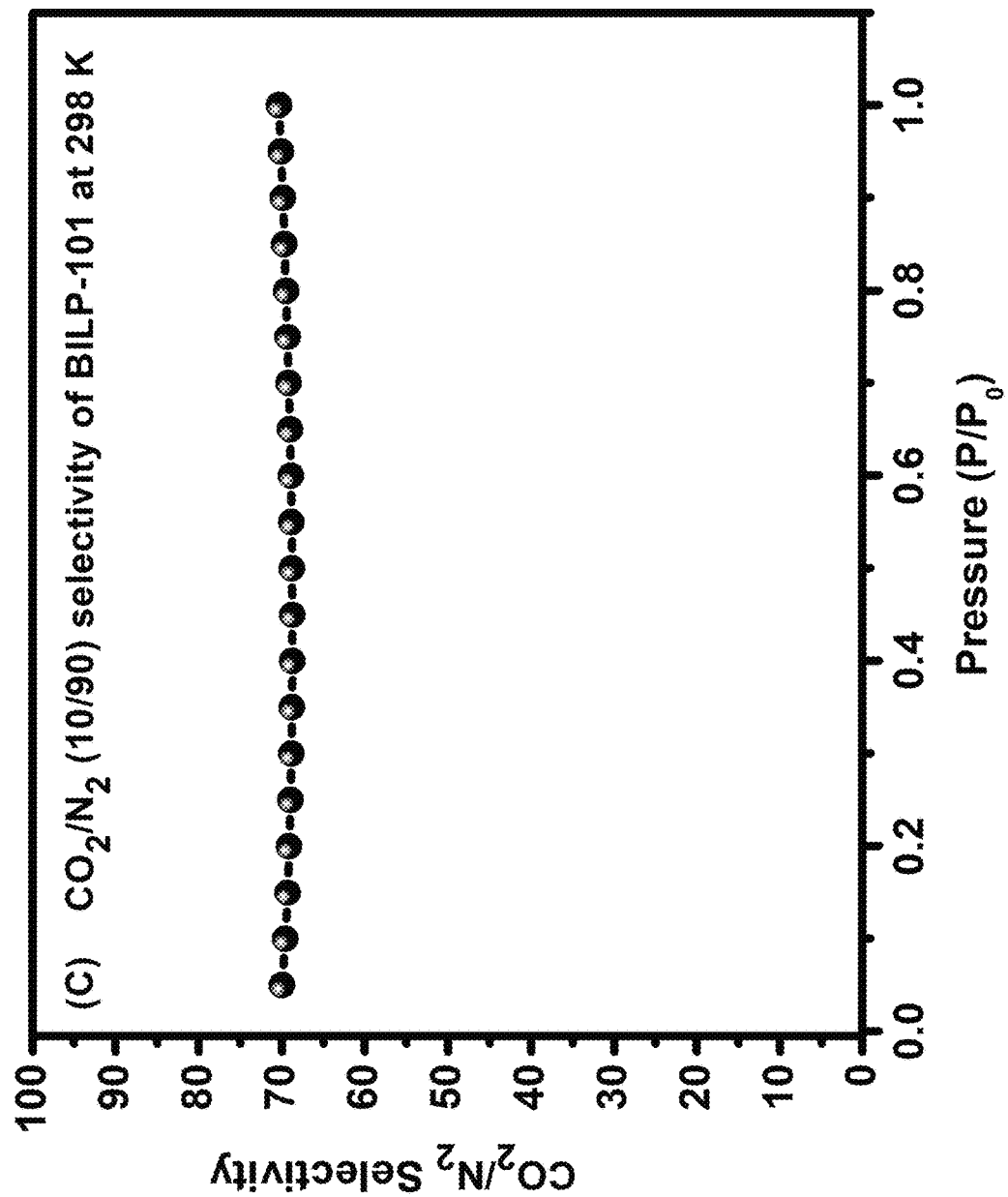
FIG. 3C is a graph depicting selectivity ratio of $CO_2$ to $N_2$ of the polymer, in accordance with features of one or more embodiments of the present invention.
Figure 6:
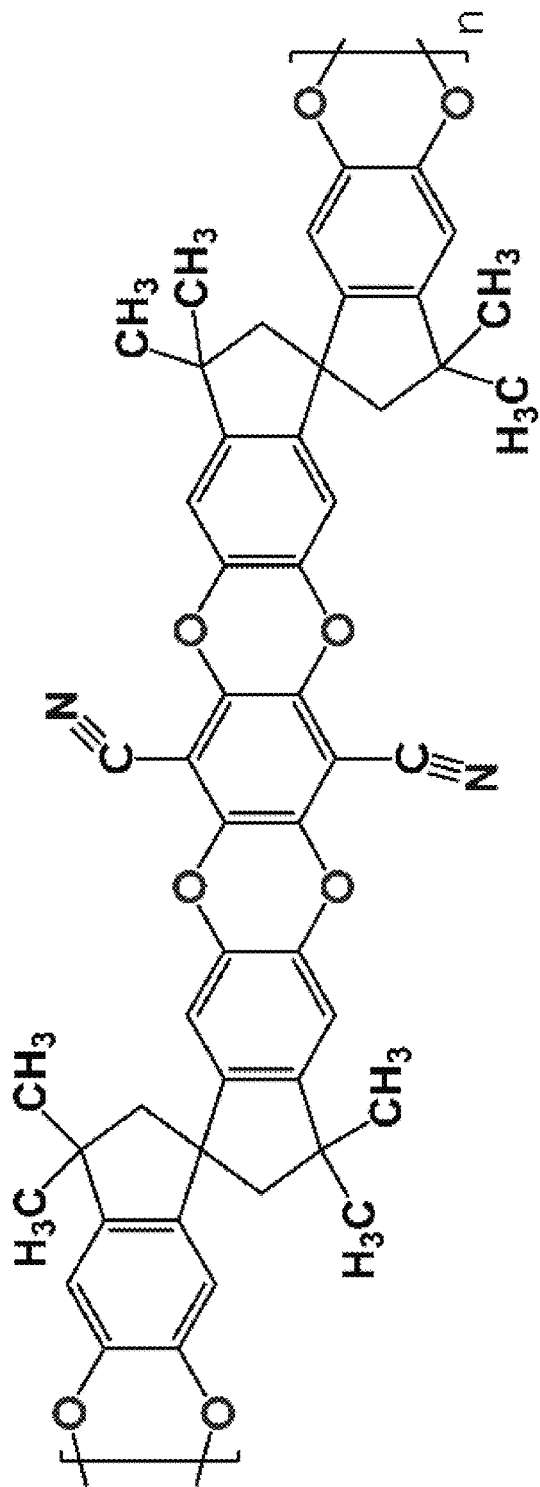
FIG. 6 is chemical structure of an organic matrix material, in accordance with features of one or more embodiments of the present invention.

FIGS. 3A-3C are graphs of data generated when the invented polymer is characterized by common spectral and analytical techniques. FIG. 3A is a graph showing $CO_2$ and $N_2$ uptake isotherms at 298 K. FIG. 3B is a graph depicting heat of adsorption for $CO_2$. FIG. 3C is a graph depicting polymer adsorption selectivity ratio of $CO_2$ over $N_2$ via IAST.

Gas sorption and uptake properties of the invention were tested using both volumetric and gravimetric sorption analysis instruments. The typical type I isotherm showed rapid $N_2$ uptake at low relative pressures ($P/P_o$<0.1 bar) as an indication of highly microporous nature of the invented polymer. The calculation of the specific BET surface areas showed that the polymer possesses around 700 $m^2 g^{-1}$ surface area.

Pore size distribution (PSD) of polymers was calculated by fitting the adsorption isotherm and with none local density functional theory (NLDFT). The pore width maxima of the polymer was 0.54 nm. Pore volumes, calculated at $P/P_o$=0.90, were 0.4 cc/g. Suitable pore volumes range from about 0.3 cc/g to about 0.8 cc/g. Narrower micropores, compared to similar porous polymers can be attributed to relatively small and rigid building blocks employed in the synthesis of the polymer. In addition, the selection of a smaller aldehyde unit resulted in a higher Lewis base N/C ratio. This enabled high $CO_2$ uptakes at low pressures as it provides more adsorption sides for the $CO_2$.

The heat of adsorption ($Q_{st}$) of the sorbent for $CO_2$ and if s binding affinity levels were investigated. $Q_{st}$ for $CO_2$ was calculated by the commonly used virial and Clausius-Clapeyron equations. The polymer showed a high $Q_{st}$ value (33 kJ $mol^{-1}$) demonstrating that the polymer can strongly bind to $CO_2$ within the physical interaction range (FIG. 3). This binding affinity endows a high $CO_2$ uptake and selectivity in the low pressure region, yet it still yields a minimal energy penalty to regenerate the sorbent while maintaining high $CO_2$ uptake and selectivity properties.

The invented polymer exhibits lower heats of adsorption energy. This leads to less energy penalty in desorption of $CO_2$. The regenerability performance of the sorbent is relatively low compared to the state of the art, such that less than about 32 kJ/mol are required for desorption. A suitable range for $CO_2$ heat of adsorption is 30-45 kJ/mole.

Five subsequent experimental $CO_2$ adsorption and desorption cycles (FIG. 4B) also show that the polymer is able to regenerate without applying any heat. Therefore, the heat of adsorption of the sorbent polymer eliminates the regeneration problems associated with current amine-solvent based carbon capture technology.

Other gas ($N_2$ and $CH_4$) uptake performances were studied for the invented polymer to characterize its preferential binding affinity and to calculate the selectivity of $CO_2$ over $N_2$ and $CH_4$. Compared to $CO_2$, the polymer shows much lower uptake for $CH_4$ and almost negligible adsorption of $N_2$. The initial slope method and IAST were applied to the selectivity calculations. Using the initial slope method, the polymer exhibited $CO_2/N_2$ selectivity of 80, outperforming all reported selectivity values for BILPs. This higher selectivity value of the invented polymer compared to other sorbents can be attributed to its higher functional group (imidazole) concentration coupled with its narrower pore size property.

A $CO_2$ isotherm of the polymer showed about 1 mmol/g (~4 wt %) at 298K and 0.15 bar. This exceeds all previously reported polybenzimidazole materials for a post-combustion flue gas scenario.

The invention reveals $CO_2$ uptake performances of the invented polymer up to 12 bars (FIG. 4A) to ensure fair comparison with similar reported porous organic polymers considered as a sorbent. The invented polymer exhibits $CO_2$ uptake of 10 wt % and 19 wt % at 298K and 1 bar and 10 bar, respectively.

FIG. 4B is a graph depicting adsorption rates of the polymer at 298 K over 5 cycles. These rates were obtained without regeneration of the polymer between cycles. Optionally, a vacuum can be applied on the samples between cycles.

$CO_2$ uptake, working capacity and regenerability properties of the invented polymer were evaluated under post combustion flue gas settings using vacuum swing adsorption. Working capacity of the invented polymer was calculated to be about 0.8 mole/kg. Suitable working capacities are between 0.35 mole/kg and 0.8 mole/kg. The CO2 working capacity of the invented sorbent (at CO2:N2) was 10:90 using vacuum swing adsorption. This working capacity was calculated by subtracting the $CO_2$ desorption capacity of the invented sorbent at 0.1 bar from its $CO_2$ adsorption capacity at 1 bar. Generally, the substrate is capable of adsorbing targeted moiety in a concentration ranging from between about 0.1 to about 0.2 bar, with 0.12 to 0.16 bar preferred.

The polymer showed an exceptional sorbent selection parameter, S, factor of 556.4. S factor is the comprehensive criteria to evaluate $CO_2$ capture properties of sorbents as it combines the working capacity, selectivity and regenerability criteria, and therefore it gives a better insight into the trade-off between selectivity and uptake. As depicted in FIG. 5, this S value is the highest in top performing sorbents considered for post-combustion flue gas separation including Zeolite 13X, Ni-MOF-74, and NoritR1 extra which were evaluated under the same settings (temperature, pressure, method).

Composite Adsorbent
Detail

Aside from being used neat as an adsorbent, the invented polymer can also be combined with other moieties to enhance its adsorbing qualities. For example, the invented porous benzimidazole-linked polymer can be combined ionically or covalently (including H-bonding) with an amine, wherein the amine resides in the pores of the polymer. Specifically, during the amine impregnation step performed by dispersing BILP-101 and amines in methanol, the imidazole sites of BILP-101 tether to primary amines through hydrogen bonding. The higher the bonding energy between the polymer and the sorbent, the higher the chemical stability ensured in the final functionalized polymer.

Given this combination, the adsorption efficiency of the composite is more than two-fold compared to that of neat polymer. Suitable amines include, but are not limited to ethylenediamine, diethylenetriamine, triethylenetetramine, polyethyleneimine, and combinations thereof. The weight ratio of the amine to the porous polymer is between approximately 10 percent and 30 percent, preferably between 15 percent and 25 percent and most preferably about 20 percent.

Mixed Matrix
Membrane Detail

The invented polymer is also combined with an organic matrix, such that the polymer resides within the matrix to form a dual phase heterogeneous membrane. Flat sheet MMMs were fabricated, but curved topographies, cylindrical structures, and other non-flat configurations may also be fabricated. Elaboration of the inventors' metal free fabrication protocol of the invented heterogeneous membranes can be found at A. *Chem. Commun.*, 2016, 79, pp. 11768-11771 the entirety of which is incorporated by reference.

The gas permeability of the fabricated MMMs were evaluated under ideal conditions and subsequently using a slip stream of actual flue gas from a pulverized coal-burning power plant.

An embodiment of this membrane comprises the invented benzimidazole linked polymer as filler material, and a polymer of intrinsic microporosity (PIM), such as those was formulated according to the teaching provided in N. B. McKeown et al, *Chem. Soc. Rev.*, 2006, 35, 675-683, the entirety of which is incorporated by reference. A suitable PIM-1 utilized was based on polydibenzodioxin. Other suitable polymeric membranes can be matrix materials, including, but not limited to soluble thermoplastic polyimide (e.g., Matrimid® by Ciba Specialty Chemicals North America, Tarrytown, N.Y.), polysulfone, and polyethylene glycol.

A highly rigid and nonlinear linking group is positioned between the phthalocyanine subunits so as to prevent structural relaxation and loss of microporosity. A suitable linking group is derived from commercially available 5,5',6,6'-tetrahydroxy-3,3,3',3'-tetramethyl-1,1'-spirobisindane. The spiro-centre (i.e., a single tetrahedral carbon atom shared by two rings) provides the nonlinear shape, and the fused structure the required rigidity.

The microporosity within the network PIMs is maintained by a network of covalent bonds.

Porosity properties of PIM-1 and BILP-101 were evaluated by N2 isotherms at 77 K using a gas sorption analyser. The Braunauer-Emmett-Teller (BET) surface area of the two polymers was calculated as 730 and 550 m2g-1 for PIM-1 and BILP-101, respectively. Both polymers featured microporosity (pore size <2 nm) as calculated by the non-local density functional theory.

PMI-1 is soluble in aprotic solvents and forms a thin film, therefore making it suitable as the polymer foundation matrix. BILP-101 nanoparticles were dispersed in chloroform and then the PIM was dissolved to form polymer solutions containing 17, 30 and 40 weight percent of BILP-101 relative to the total membrane.

The resulting MMMs were cast on a relatively inert flat substrate (such as glass) and subsequently peeled off with methanol and heated to remove any retained solvent.

FT-IR analysis showed that increasing the BILP-101 concentration in the film resulted in more N—H and hydrogen bonded peaks between 3400-354-$cm^{-1}$ and C=N bands at 1641 cm-1. These results are characteristic of stretching f the imidazole ring.

Incorporation of BILP-101 particles into the PIM film increased thermal decomposition temperature comparted to neat PIM film. Incorporation of BILP-101 into the PIM film resulted in up to a 53 percent enhancement in the CO2 permeability. Surprisingly and unexpectedly, the inventors found that the loading of BILP into the PIM films incorporates more free volume (porosity) to the resulting membrane.

Table 1 infra displays the pure gas permeability of the invented membranes using pure gases at 40 C. The permeability values are in Barrers, which is a non-SI unit of gas permeability commonly used in membrane technology.

TABLE 1

| Membrane | $CO_2$ perm | $N_2$ perm | $CO_2/N_2$ selectivity |
|---|---|---|---|
| PIM | 4700 | 240 | 19.3 |
| 17 wt % BILP | 6300 | 420 | 15.1 |
| 30 wt % BILP | 7200 | 470 | 15.3 |
| 40 wt % BILP | 5100 | 290 | 17.4 |

FIG. 7 is a chart showing the permeability and permeance of $CO_2$, $O_2$ and $N_2$ of actual flue gas from a coal fire plant. (Permeance is the degree to which a material transmits another substance.) The membrane tested comprised 30 weight percent BILP/PIM.

In summary, one or more embodiments provides a benzimidazole-linked polymer and the incorporation of porous polybenzimidazole into a polymeric film or membrane to facilitate separation of $CO_2$ from a fluid stream. The membrane exhibited several characteristics, including high chemical and thermal stability, excellent compatibility between the two microporous polymeric components (BILP and PIM) in film form, high $CO_2$ permeability, and stable performance with actual post combustion flue gas.

It is to be understood that the above description is intended to be illustrative, and not restrictive. For example, the invented polymer is applicable to the capture of a myriad of target moieties and scenarios, including post-combustion $CO_2$ separation and capture, pre-combustion $CO_2$ separation and capture, high pressure storage of light gases ($CO_2$, $CH_4$ and $H_2$). Furthermore, alternative uses of the invented polymer include as a heterogeneous catalyst, for drug delivery, rare earth element capture and separation and in optoelectronic applications In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A substrate for separating a first gas component from a gaseous mixture, said substrate comprising a benzimidazole-linked polymer which has a pore size distribution equal to or less than about 0.60 nm, wherein the benzimidazole-linked polymer has the following structural formula:

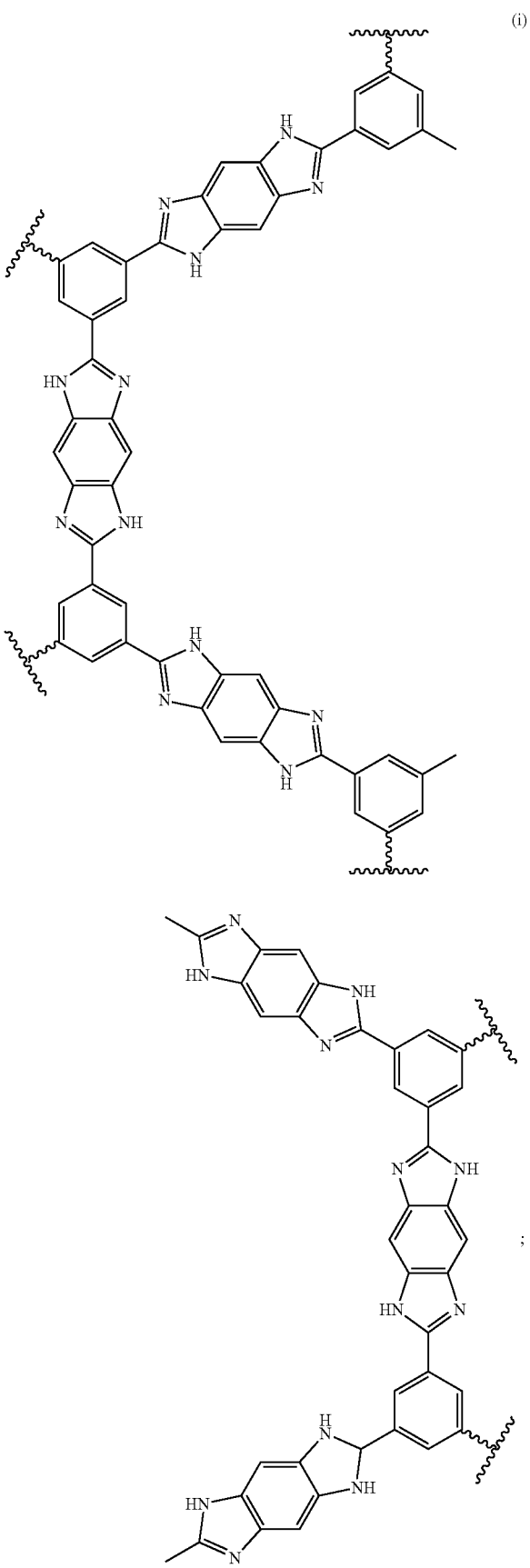

(i)

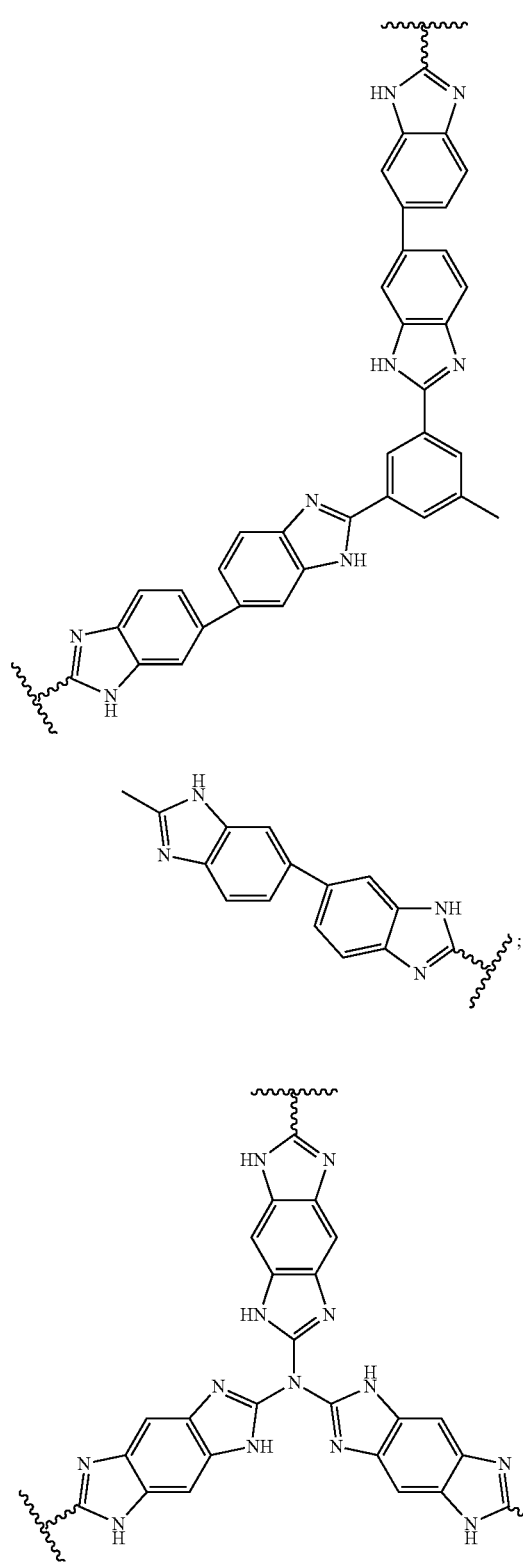

2. The substrate as recited in claim 1 wherein the first gas component is a chemical moiety selected from the group consisting of $CO_2$, $CH_4$, $H_2$, $N_2$, $C_2H_4$, and combinations thereof.

3. The substrate as recited in claim 1 wherein the first gas component is $CO_2$ and the substrate has a $CO_2/N_2$ selectivity of greater than approximately 70.

4. The substrate as recited in claim 1 wherein the first gas component is $CO_2$ and has a regeneration energy no greater than about 40 kJ/mol.

5. The substrate as recited in claim 1 wherein the polymer defines pores and amines residing within the pores.

6. A method for synthesizing a substrate for separating a first gas component from a gaseous mixture, the method comprising performing a free condensation reaction between an aryl-o-diamine and an aryl-aldehyde yielding a benzimidazole-linked polymer having a pore size distribution equal to or less than about 0.60 nm, wherein the free condensation reaction is performed between (i) 1,2,4,5-benzenetetramine tetrahydrochloride and benzene-1,3,5-tricarbaldehyde, (ii) [1,1'-biphenyl]-3,3'4,4'-tetraamine and benzene-1,3,5-tricarbaldehyde, or (iii) 1,2,4,5-benzenetetramine tetrahydrochloride and N,N-diformylformamide.

7. The method as recited in claim 6 wherein the substrate is produced in a single reaction vessel.

8. The method as recited in claim 6 wherein the reactants are template free.

9. The method as recited in claim 6 wherein secondary and tertiary amines are supplied by imidazole.

10. The method as recited in claim 6 wherein the substrate has a nitrogen to carbon molar ratio of up to about 68:24.

11. The method as recited in claim 6 wherein no metal catalyst is required.

12. A $CO_2$ separation membrane comprising a benzimidazole-linked polymer residing within a matrix, wherein the benzimidazole-linked polymer has a pore size distribution equal to or less than about 0.60 nm and has the following structural formula:

(i)
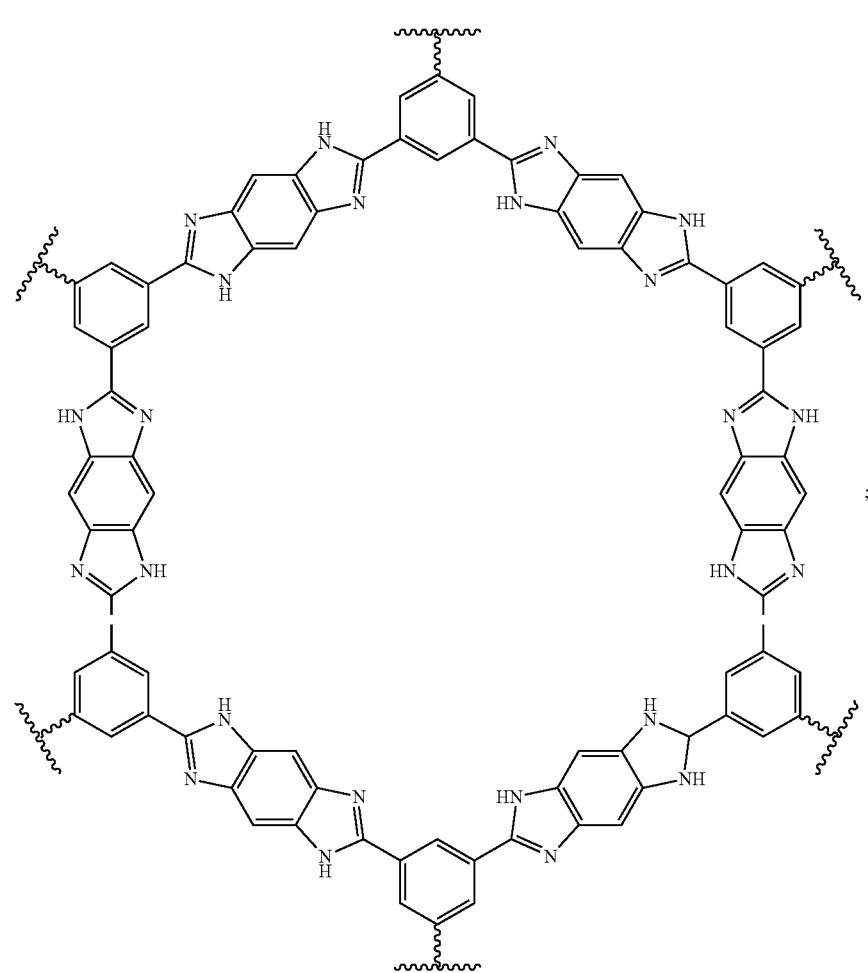
;
(ii)
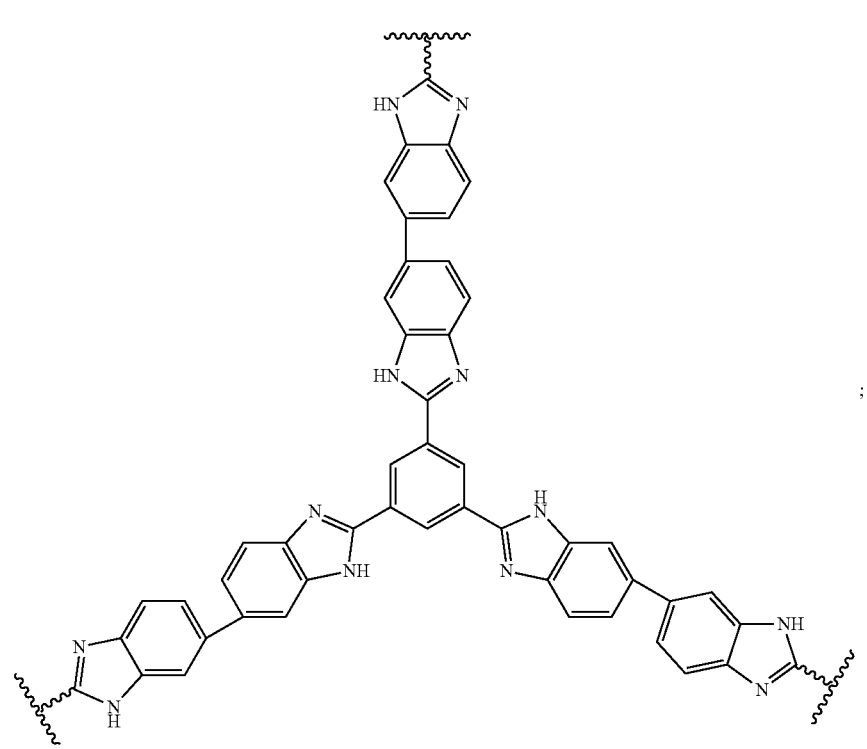
; or

-continued (iii)

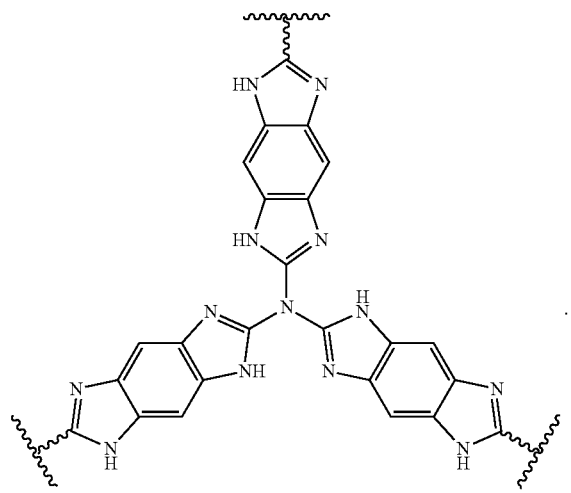

13. The membrane as recited in claim 12 wherein the matrix is a microporous polymer of polydibenzodioxin.

14. The membrane as recited in claim 12 wherein between 10 and 40 weight percent of the membrane is the benzimidazole-linked polymer.

15. The membrane as recited in claim 12 wherein the membrane display a $CO_2$ permeability of greater than 6000 Barrer.

16. The membrane as recited in claim 12 wherein the membrane has a $CO_2/N_2$ selectivity greater than 15.

17. The membrane as recited in claim 12 wherein the matrix is a polymer selected from the group consisting of phthalocyanine, polyimide, polysulfone, polyethylene glycol and combinations thereof.

* * * * *